United States Patent
Ramprasad et al.

[11] Patent Number: 5,208,335
[45] Date of Patent: May 4, 1993

[54] REVERSIBLE OXYGEN SORBENT COMPOSITIONS

[75] Inventors: Dorai Ramprasad; Guido P. Pez, both of Allentown; Ronald M. Pearlstein, Macungie, all of Pa.; Ingrid K. Meier, Asbury, N.J.

[73] Assignee: Air Products and Chemicals, Inc., Allentown, Pa.

[21] Appl. No.: 890,065

[22] Filed: May 27, 1992

Related U.S. Application Data

[63] Continuation-in-part of Ser. No. 672,711, Mar. 19, 1991, Pat. No. 5,126,466.

[51] Int. Cl.$^5$ .............................................. C07F 15/06
[52] U.S. Cl. ........................................ 544/225; 546/2; 556/118; 556/138; 556/140
[58] Field of Search ................... 556/118, 138, 140; 544/225; 546/2

[56] References Cited

U.S. PATENT DOCUMENTS

| | | | |
|---|---|---|---|
| 3,980,763 | 9/1976 | Mullhaupt | 423/579 |
| 4,251,452 | 2/1981 | McAuliffe | 260/429 |
| 4,477,418 | 10/1984 | Mullhaupt et al. | 423/219 |
| 4,830,999 | 5/1989 | Drago et al. | 502/74 |

OTHER PUBLICATIONS

R. S. Drago et al., "Entrapment of an Anionic Stable Moisture-Resistant Oxygen Carrier in Zeolite Y", J. Amer. Chem. Soc., 110, p. 304, (1988).
G. A. Kozlov et al., "Structure and Properties of the Products of Reaction Between Molecular Oxygen and New Salts of Pentacyapnocobaltate (II) Anion," Translated from Teoreticheskayadiaks Eperimental'naya Khimiya, 17, (5) 686 1983.
S. Imamura, et al., "Separation of Oxygen from Air by [Co$_{II}$(bpy)(terpy)]$^{2+}$Complexes in Zeolite Y", Langmuir 1985, 1, 326–(1985).
R. J. Taylor et al., "Characterization of a Cobalt (II) Cyanide Complex Inside Zeolite Y that Reversibly Binds Oxygen", J. Amer. Chem. Soc., 111, 6610, (1989).
S. J. Carter, et al., "Cobalt (II) Cyanides in Aprotic Media: Effect of Varying Counterino and Solvent", Inorg. Chem., (1986), 25, 2888-2894.
S. J. Carter, "Synthesis, Characterization and Reactions of New Organocyanocobaltates", Thesis Brandeis University, 1988.
J. H. Hildebrand, "The Thermal Dissociation of Barium Peroxide", J. Amer. Chem. Soc., 34, p. 246, (1912).

*Primary Examiner*—José G. Dees
*Assistant Examiner*—Porfirio Nazario
*Attorney, Agent, or Firm*—Mark L. Rodgers; William F. Marsh; James C. Simmons

[57] ABSTRACT

High Capacity solid state cyanocobaltate complexes represented by the chemical formula:

$$[(A)_a(R_4N)_b]^{z+}{}_{x/z}[Co(CN)_n]^{x-} \cdot pS$$

where:
A is alkali metal atom, alkaline earth metal atom, Zn, Cd or Hg atom;
a is any number from 0 to 2.5
each R is independently $C_1$-$C_{10}$ substituted or unsubstituted alkyl, aryl or aralkyl; or a long chain hydrocarbon polymer
b is any number from greater than zero to 3
z is 1, 2 or 3;
n is any number from 3 to 5;
x is n−2;
p is any number from greater than zero to 6; and
S is a ligand which is capable of coordinating with $[(A)_a(R_4N)_b 9^{z+}$, Co or both.

are capable of chemically binding oxygen to form novel oxygen adducts, thereby selectively removing oxygen from an oxygen-containing fluid stream. The bound oxygen may be recovered from the complexes by increasing the temperature or by reducing the partial pressure of $O_2$ above the adduct.

14 Claims, No Drawings

REVERSIBLE OXYGEN SORBENT COMPOSITIONS

CROSS REFERENCE TO RELATED APPLICATION

This is a continuation-in-part of copending application Ser. No. 07/672,711 filed Mar. 19, 1991, now U.S. Pat No. 5,126,466, which is hereby incorporated by reference.

TECHNICAL FIELD

The present invention relates to materials which are useful for the selective separation and recovery of oxygen from air or other oxygen-containing fluid streams.

BACKGROUND OF THE INVENTION

Gas separations may be carried out by a number of methods including distillation at cryogenic temperatures, the use of permselective membranes and by processes that utilize compositions that can reversibly and selectively sorb a component of the gas mixture. For sorption-based separation of air, current commercial technologies utilize zeolite molecular sieves as $N_2$-selective adsorbents and carbon molecular sieve (CMS) materials as $O_2$-selective adsorbents. These technologies, which are usually employed for the production of enriched nitrogen or oxygen, (rather than very high purity N2 or $O_2$) have several inherent limitations which restrict their competitiveness against the cryogenic and membrane separation methods.

Synthetic zeolites reversibly adsorb nitrogen in preference to oxygen. When used for instance in a pressure-swing adsorption (PSA) process for the separation of air, the zeolite bed selectively takes up the nitrogen which is recovered by de-pressurization or evacuation of the bed. The drawback in this separation method is that it is performed inefficiently by adsorbing nitrogen which is the major component of air.

The potential advantages of selective oxygen sorbents have long been recognized and there has been much research effort directed at the synthesis of suitable materials. At the present time carbon molecular sieve (CMS) kinetically oxygen selective adsorbents are used in PSA air separation processes for the production of either enriched $N_2$ or $O_2$. Several factors limit the productivity and hence the cost-effectiveness of this technology. Even the most effective current CMS sorbents have a poor working $O_2/N_2$ selectivity in the PSA process. The necessarily short cycle times of the PSA process and the limiting oxygen adsorption kinetics lead to a poor utilization of the adsorption bed.

U.S. Pat. No. 4,477,418 discloses solid state transition metal hexacyano compounds (cyanometallates) defined as $M_x[M'(CN)_6]_y$ where M=Sc, Mn, Fe, Co, Ni etc and M' is strictly Cr, Mn, Fe, Co which the selective oxygen sorbents which are taught to be useful in processes for the separation of oxygen. The hexacyanometallate solids can be microporous, containing very small voids within their structures. In certain cases, depending on the specific formula, when the voids are of molecular dimensions the compounds have been described as "molecular sieves" since only molecules that are less than a certain effective diameter are adsorbed within their structures. The experimental data presented in U.S. Pat. No. 4,477,418 show that a number of the listed hexacyanometallates exhibit $O_2$ versus $N_2$ adsorption selectivity. Selectivity is seen at short contact times but also, to a lesser extent, at apparent equilibrium conditions. Among the compositions studied there are wide variations in both the time-dependent (i.e. kinetic) and equilibrium values of the oxygen loading, $O_2/N_2$ selectivity (ratio of oxygen to nitrogen loading) and in the kinetics of oxygen adsorption. The data show an approximate inverse relationship between the rate of oxygen uptake and the $O_2/N_2$ selectivity which is consistent with a molecular sieving or size-selective physical adsorption process, one which is more favorable for entry of the smaller $O_2$ molecule.

A relatively limited number of solid state chemical $O_2$-selective sorbents are known. One of the oldest is the barium oxide/peroxide system disclosed by J. H. Hildebrand, J. Amer. Chem. Soc., 34, 246 (1912), which on the basis of the reversible equilibrium: $BaO + \frac{1}{2} O_2 \rightleftharpoons BaO_2$ at about 600° C. was once used in an industrial process for the separation of air. U.S. Pat. No. 3,980,763 discloses praseodymium oxide materials which bind $O_2$, converting it to an oxide ($O^{2-}$) ion. The process is temperature/pressure reversible at about 400° C.–500° C., and is said to have the advantage over $BaO_2$ of not being deactivated by atmospheric carbon dioxide. It is taught in U.S. Pat. No. 4,251,452 that solid manganese phosphine complexes reversibly absorb oxygen, however, the number of reversible oxygen adsorption and desorption cycles that can be obtained appears to be quite limited.

Solid state compositions prepared by an entrapment or encapsulation of a metal complex within the cage of a synthetic zeolite have been shown to function as reversible oxygen sorbents. R. S. Drago, et al., J. Amer. Chem. Soc., 110, 304 (1988) and U.S. Pat. No. 4,830,999 both teach entrapment of the anionic cobalt(II) cyanide (cyanocobaltate(3-)) complexes as ion-paired species: $A^+_3[Co(CN)_5]^{3-}$ or possibly $A^+_2[Co(CN)_4]^{2-}$ ($A^+$ is $Na^+$, $Cs^+$, etc.) within the pores of a crystalline aluminosilicate zeolite, to yield solid state $O_2$-selective sorbents. While the compounds $A^+_3[Co(CN)_5]^{3-}$ dissolved in water or polar organic solvents are well known to bind oxygen (giving either superoxo or peroxo complexes, depending on conditions), the $O_2$-binding is always considered to be irreversible (Ref. G. A. Kozlov, et al., i Teoreticheskaya Eksoerimental'naya Khimiva, 17 (5) 686 (1984)). Thus for example, heating the superoxo complex, $[NEt_4]^+_3[O_2Co(CN)_5]^{3-}$, at 120° C. in vacuo gives only a mixture of decomposition products: $O_2$, $CO_2$, butene and other hydrocarbons. The observed reversible binding of $O_2$ by the same monomeric anionic complex in the zeolite, as described in U.S. Pat. No. 4,830,999, is attributed to as yet uncharacterized interactions between the complex and the walls of the zeolite cavity in which it resides. These interactions significantly change the nature (effectively alter the composition) of the complex such that it becomes reversibly $O_2$-binding.

While the entrapment of oxygen-carrier complexes in zeolites affords $O_2$-selective solid sorbents, there are significant disadvantages in this technique. Because of the need to incorporate (usually by ion-exchange methods) $Co^{2+}$ ions as well as the accompanying organic ligands (eg SALEN, $CN^-$, etc.) in zeolite cages of fixed and usually very small dimensions, and also at the same time retain a certain degree of "openness" within the structure for facile accessibility by $O_2$, the practical loading level of the active $O_2$-binding Co(II) species is often quite small. Thus, as taught by S. Imamura, et al.,

*Langmuir,* 1, 326 (1985), in [Co$^{II}$(BPY)(TERPY)]-LiY, cobalt complex in LiY zeolite composition, the concentration of Co$^{II}$ active centers is only $1.05 \times 10^{-2}$ mmole/g of zeolite (giving a capacity of about 0.022 cc O$_2$/g). In the case of the Co(CN)$_5^{3-}$/Co(CN)$_4^{2-}$ in zeolite Y sorbent, although a relatively high concentration of Co$^{+2}$ (up to 7.1 wt % or 1.2 mmoles/g) can be incorporated, by spectroscopic measurements less than 1% of this cobalt is in an active O$_2$-binding configuration (Ref. R. J. Taylor, et al., *J. Amer. Chem. Soc.,* 111, 6610 (1989)). The second drawback of zeolite entrapped metal complex sorbents is their relatively high "background" adsorption capacity for N$_2$ which limits their O$_2$/N$_2$ selectivity in air separation applications. While the Co(CN)$_5^{3-}$/Co(CN)$_4^{2-}$ sorbent in zeolite Y at 40 torr pressure has a selectivity ($\alpha$O$_2$/Ar) of ~1.3 on the basis of data given in the above reference, the sorbent's oxygen to nitrogen selectivity, (because of the high natural adsorptivity of the latter), is calculated to be less than 1; ie, about 0.7.

The objective in the art has been to develop easily synthesized solid state metal complex oxygen carriers which have a rapid reactivity and a high reversible equilibrium capacity for oxygen and a relatively low affinity for nitrogen. Additionally, such adsorbents should retain these properties in O$_2$ recovery applications over a long period of time. Prior to the present invention, no process has been taught which employs adsorbents which meet all of the above qualifications.

S. J. Carter, et al., *Inorg. Chem.* 25, 2888–2894 (1986) disclose the synthesis of what they believed to have been Li$_3$[Co(CN)$_5$]·3DMF, although they were unable to purify the material produced in their synthesis reaction. This reference teaches the use of this complex for cyanation reactions, and it is specifically stated that, based upon the research presented in the article, this compound would not be the preferred choice for such reactions. No mention is made of the suitability of this or any similar compound for reversibly binding oxygen. Carter also reported similar findings in a thesis entitled "Synthesis, Characterization and Reactions of New Organocyanocobaltates" Brandeis University, 1988.

SUMMARY OF THE INVENTION

Solid state composition comprising one or more cyanocobaltate complexes represented by the chemical formula $$[(A)_a(R_4N)_b]^{z+}{}_{x/z}[Co(CN)_n]^{x-} \cdot pS$$

where:
  A is alkali metal atom, alkaline earth metal atom, Zn, Cd or Hg atom;
  a is any number from 0 to 2.5
  each R is independently C$_1$-C$_{10}$ substituted or unsubstituted alkyl, aryl or aralkyl; or a long chain hydrocarbon polymer
  b is any number from greater than zero to 3
  z is 1, 2 or 3;
  n is any number from 3 to 5;
  x is n−2;
  p is any number from greater than zero to 6; and
  S is a ligand which is capable of coordinating with $[(A)_a(R_4N)_b]^{z+}$, Co or both.

are capable of selectively binding (i.e., sorbing) oxygen thereby making them useful for removing oxygen from oxygen-containing fluid streams. These complexes operate by chemically reacting with oxygen to form oxygenated stable complexes which are the corresponding oxygen adducts of the above cyanocobaltate complexes.

The above described process for selectively binding or sorbing oxygen can be reversed to cause the release of the bound oxygen to regenerate the complex and recover the oxygen. This can be achieved by heating the adduct or by any means which reduces the partial pressure of O$_2$ above the adduct, such as evacuating or passing a sweep gas over the adduct.

The above cyanocobaltate complexes are advantageous over prior art oxygen sorption materials in that the present solid state materials rapidly sorb oxygen, and even at equilibrum have a high capacity and selectivity for oxygen over nitrogen and other gases. This is due in part to the fact that these cyanocobaltate complexes have a reversible chemical affinity for oxygen, rather than relying primarily on their physical characteristics for adsorbing oxygen as is the case with zeolites and carbon molecular sieves. This chemical binding reduces or eliminates problems encountered in prior processes relating to kinetically dependent adsorption and poor adsorption at or near equilibrium conditions. An additional advantage in using the present complexes is that they can be used in a non-aluminosilicate environment (ie, they do not have to be encapsulated in the cage of a zeqlite) to reversibly bind oxygen.

DETAILED DESCRIPTION OF THE INVENTION

We have found that certain solid state cyanocobaltate complexes chemically react with oxygen to selectively sorb the gas and thus permit its separation and recovery from air or other fluid mixtures. The complexes are solid state materials wherein the active reversible O$_2$-binding species are anionic, pentacyano-, tetracyano- and lower cyanide coordination number complexes of cobalt. The process is operated by simply bringing an oxygen-containing fluid stream into contact with the solid state complexes, such as in typical temperature or pressure swing adsorption processes, although the present process can be used in any separation process designed for separating and/or scavenging oxygen, even in trace amounts, from a gas stream or from a liquid in which oxygen has been dissolved. Specific applications for this type of process include the separation of oxygen from gas streams containing oxygen and nitrogen, such as air, and for the separation of trace amounts of oxygen from a stream comprising predominently nitrogen or argon. Such a process is advantageous over prior art separation processes in that solid state complexes are used which reversibly bind oxygen, thereby allowing the sorbed oxygen to be recovered, and the sorbent (complex) to be regenerated by heating or by reducing the O$_2$ partial pressure over the adduct.

The oxygen-reactive sorbents used in the process are cyanometallates of cobalt(II) which contain at least three but not more than five cyanide ligands around the cobalt central metal atom ions, and which can be represented by the chemical formula:

$$[(A)_a(R_4N)_b]^{z+}{}_{x/z}[Co(CN)_n]^{x-} \cdot pS$$

where:
  A is alkali metal atom, alkaline earth metal atom, Zn, Cd or Hg atom;
  a is any number from 0 to 2.5
  R is C$_1$-C$_{10}$ substituted or unsubstituted alkyl, aryl or aralkyl; or a long chain hydrocarbon polymer
  b is any number from greater than zero to 3 z is 1, 2 or 3;

n is any number from 3 to 5;

x is $n-2$;

p is any number from greater than zero to 6; and

S is a ligand which is capable of coordinating with $[(A)_a(R_4N)_b]^{z+}$, Co or both.

In the above structural formula, cyanide is ligated to cobalt through carbon while n, the number of cyanide ligands per cobalt atom ranges from a maximum of 5 to a minimum of 3. Since the formula represents an overall composition of a complex solid-state structure which may contain different $[Co(CN)_n]^{x-}$ units (depending on the value of n), n in the above formula may be a fractional number. The cationic portion of the complex contains an $R_4N$ cation, wherein each R is independently a $C_1-C_{10}$ substituted or unsubstituted alkyl, aryl or aralkyl group (although all four R groups cannot be aryl) or, alternatively, R can be a long chain hydrocarbon polymer such that $R_4N$, for example can be a nitrogen containing polymer such as Amberlyst. Optionally, the cation portion of the complex may also contain a second cation, A, which is an alkali, alkali earth, Zn, Cd or Hg atom. The total cationic portion, $[(A)_a(R_4N)_b]^{z+}{}_{x/z}$, may also constitute two or three different cations with z separately ranging from 1 to 3, the number and total charge of the cations being so chosen as to maintain overall electrical neutrality for the structural formula.

The cobalt central metal ion in the above formula is in a divalent state, thus $x=n-2$. Since, however, there is the possibility that the overall composition expressed by the above formula contains $[Co(CN)_n]^{x-}$ units with different values of n, n and x in the formula may be fractional numbers.

In the formula, S represents a ligand, or several different ligands, of total number p, wherein p may be any number greater than zero and up to 6, including fractions since more than one structure represented by the above formula may be combined to form the total complex. These ligands (S) may coordinate to the $A^{z+}$ ion or to the cobalt ion (but only when n <5), or both.

Representative examples of S when the ligand is bound to the $A^{z+}$ ion include: N,N-dialkyl formamides (preferably DMF), N,N-dialkylamides and alkyl lactams (preferably N,N dimethylacetamide, N-methyl-2-pyrrolidinone and N-methyl piperidone), N-alkyl imides such as N-methyl succinimide, ammonia and potentially chelating tertiary amines such as N,N,N',N'-tetramethyl ethylenediamine and hexamethylenetetramine, as well as organic carbonates, acetone, sulfur-oxygen, and phosphorus-oxygen compounds.

Representative examples of S when the ligand is bound to the cobalt atom include: N-heterocycles such as pyridine, alkyl or perfluoroalkyl ring-substituted pyridines, N-methylimidazole and 1,2; 1,3 and 1,4 -diazines; bipyridyls and alkyl or perfluoroalkyl ring-substituted dipyridyls; pyrazine, organic nitriles such as dicyanogen, N≡C—C≡N, acetonitrile, benzonitrile, t-butylnitrile, and dicyanoalkanes: N≡C(CH$_2$)$_n$C≡N where n'=1 to 4; cyanamides such as the cyanamide or dicyanamide anion, N≡C—N—C≡N; the dicyanomethane (anion), N≡C—CH—C≡N; polymers containing polyvinyl pyridine or pyrrolidone; and halide and pseudohalide ions such as Cl$^-$, F$^-$, SCN$^-$, and NCS$^-$.

Where appropriate, the above ligands may be halogenated, in particular fluorinated, for greater stability towards oxidation, or additionally, may be polymeric analogues of any of the above. While it is required that there be some ligand (S) bound to the complex, additional molecules corresponding to any of the above compounds may be present as unbound solvate molecules.

These compositions are generally prepared by reacting a cobalt(II) halide or pseudohalide with an alkali metal or alkaline earth cyanide salt in a molar ratio of $1Co^{2+}$:$nCN^-$, in a polar solvent (usually corresponding to the ligand (S) in the formula). Solids thus formed may be per se reactive towards $O_2$ or may be activated for reversible binding of $O_2$ by judicial heating or drawing a vacuum to expel a portion of the ligand S, or altering the ligands by solvent replacement. Compositions containing divalent or trivalent ($z=2,3$) ions may be prepared by the direct reaction of Co(II) halides with cyanide compounds of these ions or by metathetical reactions of solutions containing $[Co(CN)_n]^{x-}$ species with suitable sources of the cations.

In the present process, these compositions act as chemical sorbents for oxygen wherein the sorbed oxygen is attached to the cobalt(II) to form the oxygen adduct of the solid-state cyanometallate complex. Chemical bonding of oxygen with these complexes to form the oxygen adducts of the respective complexes is accompanied by changes in the UV/visible spectrum of the complex, the appearance of an O—O stretching frequency ($\nu_{O-O}$) which is significantly lower than that of free gaseous (or physically adsorbed) oxygen, and also by a "blue shift" in the $\nu_{CN}$ vibration. These analytical techniques were used to determine that, unlike the prior art hexacyanometallates, the compositions used in the present process chemically and reversibly bind oxygen. Without being bound by theory, it is believed that the ability of the complexes used in the present process to reversibly bind oxygen is made possible by reducing the electron density on cobalt through the use of countercations $[(A)_a(R_4N)_b]^{z+}$ which are able to interact with the nitrogen of the cyanide ligand to form $Co^{II}$-CN-$A^{z+}$-NC-$Co^{II}$ linkages The effect is moderated by the use of coordinating ligands S which by binding to the cation can weaken the -CN-$A^{z+}$ interaction. By thus controlling the electron density on cobalt not only is the binding of $O_2$ onto the $[Co^{II}(CN)_n]^{x-}$ unit rendered reversible, but its affinity for oxygen (i.e., the equilibrium binding constant for $O_2$) may be predictably altered.

The metal complex selective $O_2$-sorbent compositions are especially suitable for use in both pressure swing absorption (PSA) and temperature swing absorption (TSA) processes for the separation of air to recover oxygen or nitrogen or both.

In the pressure swing method, air (preferably dry) at ambient temperature and at pressures ranging from 1 to about 10 atm is passed through a column containing a fixed bed that is packed with the above cyanocobaltate solid absorbents. Oxygen is selectively absorbed by the packed bed resulting in an effluent of nearly pure nitrogen. The absorbent may take up as much as 2.3 mmoles of $O_2$ per gram. At the end of this absorption step the resulting oxygenated solid in the bed has to be regenerated. This may be done by lowering the pressure of the atmosphere above the absorbent bed to about ambient conditions or by partially evacuating it to subambient pressures as low as 0.05 atm. Alternatively, the desorption may be achieved by depressurizing the bed followed by purging it with some of the product nitrogen. The PSA methods described here may be used for the large scale production of oxygen or nitrogen from air, but are also useful for the removal of residual low levels of oxygen from nitrogen, argon and other gases that are inert to the cyanocobaltate absorbents.

In the temperature-swing method an oxygen-containing gas mixture, preferably a dry mixture, at from about 1 to 10 atm is passed through the absorbent column which results, as above, in a selective absorption of oxygen. In this case however, the regeneration of the absorbent is accomplished by heating. The desorption of $O_2$ may be assisted by also reducing the effective partial pressure of $O_2$ in the atmosphere above the absorbent by depressurization, partial evacuation to 0.1 to 0.3 atm, or by sweeping the bed with a pre-heated stream of some of the inert gas product. The latter is essentially a combined PSA/TSA process. Specific examples of PSA and TSA processes (though not with equilibrium $O_2$-selective sorbents) have been well described in the art.

In all of these processes the cyanocobaltate complexes are in the solid state and can be used in various forms such as powders, as single crystals, as pellets, as a slurry, or any other suitable form for the particular application.

The resultant oxygen adducts of the cyanometallate complexes which are formed during this process are unique structures which can be represented by the general chemical formula:

$$[(A)_a(R_4N)_b]^{z+}{}_{x/z}[Co(CN)_n \cdot O_2]^{x-} \cdot pS$$

where A, a, R, b, z, x, n, p and S are the same as set out above for the corresponding cyanocobaltate complexes. While the above chemical formula shows one oxygen molecule associated with the complex as written, there may, in some instances, be less than one oxygen molecule per this portion of the comlex since the overall composition may contain more than one of the above structural units with a single oxygen molecule bound to several such units.

The following examples are presented to better illustrate the present invention and are not meant to be limiting.

EXPERIMENTAL

In the following Examples all chemical synthesis and oxygen sorbent handling operations were done (unless otherwise indicated) under cover of nitrogen or argon using standard Schlenk line, high vacuum line, or inert atmosphere dry box techniques. Reaction solvents were carefully dried and purified by distillation from $CaH_2$ (N,N-dimethylformamide, (DMF)), or from sodium benzophenone ketyl(diethyl-ether). Thermogravimetric (TGA) analysis experiments were carried out using Perkin Elmer TGS2 and DuPont 2950 instruments, which were equipped for performing measurements in either an $N_2$ or $O_2$ atmosphere. Infrared spectra were taken using a Nicolet 510 or a Perkin-Elmer 6000 series FTIR spectrometer; the reported vibrational frequencies are considered to be accurate to within $\pm 2 cm^{-1}$.

EXAMPLE 1

Preparation of $(Et_4N)_{0.5}$ $Li_{2.5}$ $Co(CN)_5 \cdot 1.6$ (acetone)

This complex was prepared via ion exchange between solid $(Et_4N)_3$ $Co(CN)_5$ and an excess of Lithium triflate dissolved in solution. The complex $(Et_4N)_3$ $Co(CN)_5$ (0.27g. 0.465 mmole) was added as a solid to 50 ml of acetone containing (0.55 g, 3.5 mmole) Lithium triflate. The solution was stirred overnight. Even within an hour, the yellow $(Et_4N)_3$ $Co(CN)_5$ was observed to turn green because of ion exchange of the $Et_4N^+$ moeity with $Li^+$. After 18 hours the yellow green solid was filtered, washed with ether and dried. Yield=0.10 g. An infrared spectrum of this material showed that the cyanide bands were heavily split with bands at 2093, 2099, 2106, 2116 cm-1 The coordinated acetone peaks at $\sim 1650$ cm-1 were also heavily split. This may indicate a non uniform material due to differing amounts of acetone in various parts of the solid.

Elemental analysis: Calcd for $(Et_4N)_{0.5}$ $Li_{2.5}$ $Co(CN)_5$ 1.6 (acetone)

Calcd: C, 45.3; H, 5.06; N, 21.06; Li, 4.74; Co, 16.1
Found for the same batch:
C, 43.65; H 5.76; N, 21.84; Li, 4.51; Co, 15.4
C, 43.33; H 5.73; N, 20.77; Li, 4.51; Co, 15.4
Li : Co=2.5:1

Oxygen Reactivity of $(R_4N)_{0.5}$ $Li_{2.5}$ $Co(CN)_5 \cdot 1 \cdot 6$ (acetone)

This solid complex was found to reversibly bind $O_2$, although the rate of $O_2$ uptake was relatively slow. A sample of this solid was loaded on a Perkin Elmer T. G. A. and $O_2$ was introduced. A 1.75% uptake was observed in 37 minutes. This desorbed 1.74% in 560 minutes, and showed similar uptake on resorption of $O_2$ (1.93% in 45 minutes).

EXAMPLE 2

Preparation of $(Et_4N)_{0.57}$ $Na_{2.43}$ $Co(CN)_5 \cdot 2.25$ DMAC

A solution of $NaPF_6$ (0.33 g) in 50 ml DMAC was prepared. To this the complex $(Et_4N)_3$ $Co(CN)_5$ (0.15 g) was added as a solid, and the solution was stirred overnight. An aquagreen precipitate was filtered washed with DMAC (10 ml) and ether (20 ml). The infrared spectrum of this solid showed cyanide bands at 2107 $cm^{-1}$ (s), 2125 and a strong peak at 1614 $cm^{-1}$ due to DMAC. A peak at 784$cm^{-1}$ seemed to indicate residual $Et_4N^+$. An elemental analysis of this complex gave Na, 10.48%, Co, 11.4%, which is a Na: Co ratio of 2.43 : 1. This was fitted to the formula shown above and the amount of DMAC attached to the sample was confirmed by heating to 160C and measuring the weight loss.

Oxygen reactivity of the complex

This complex was loaded on a Perkin Elmer T. G. A. and cycled with 5 min $O_2$/30 min $N_2$

| Cycle No | % Uptake |
| --- | --- |
| 1 | 0.59 |
| 2 | 0.39 |
| 3 | 0.27 |

The above results show that this complex reversibly sorbed oxygen, although the reversibility was rather poor, possibly due to rapid loss of solvent.

EXAMPLE 3

Preparation of $(Et_4N)_{1.5}$ $Mg_{0.75}$ $Co(CN)_5$ 0.5 DMF

The complex $(Et_4N)_3$ $Co(CN)_5$ (0.27 g.) was dissolved in 30 ml of acetonitrile. To this was added 15 ml of DMF in which was dissolved 0.075 g of Magnesium triflate. A green solution was obtained. Addition of 50 ml ether gave a cloudy solution. A yellow green precipitate was filtered and this was washed with ether followed by acetone and then ether again. Yield =0.13 g.

An infrared spectrum of this sample showed a strong cyanide band at 2105 cm$^{-1}$, and a peak at 784 cm$^{-1}$ indicated the presence of the Et$_4$N$^+$ moiety, and a peak at ~1650 cm$^{-1}$ for DMF. A metals analysis for a bulk sample gave 13.2% Co, 4.13% Mg which is a Mg : Co ratio of 0.75 to 1. The C, H, N analysis of batches of this material were observed to fluctuate even within the same sample indicating possibly non uniform distribution of solvent. However, one batch gave an acceptable C, H, N analysis.

Calcd for (Et$_4$N)$_{1.5}$ Mg$_{0.75}$ Co(CN)$_5$ ·0.5 DMF
Calcd: C, 50.60; N, 22.34; H, 7.63; Co,13.42; Mg, 4.15
Found: C, 51.06; N, 21.46; H, 7.55; Co, 13.2; Mg, 4.13

Oxygen reactivity of the Magnesium complex

A sample was loaded on a Perkin-Elmer T. G. A. and cycled with O$_2$/N$_2$ 5 min, 10 min, respectively.

| Cycle No | % Uptake |
| --- | --- |
| 1 | 1.11 |
| 13 | 0.83 |
| 25 | 0.61 |
| 39 | 0.54 |
| 60 | 0.48 |

Both sets of cycle data indicate that the complex of this example reversibly bound oxygen.

EXAMPLE 4

Synthesis of (Bu$_4$N)$_2$Co(CN)$_4$ · C$_5$H$_5$N:

(Bu$_4$N)$_2$Co(CN)$_4$ (0.242 g, 0.373 mmol) was dissolved in anhydrous pyridine (3 mL); a light green solution resulted. After five minutes at room temperature, anhydrous hexane (10 mL) was added to precipitate a greenish-yellow solid. The solid was filtered and washed thoroughly with hexane (3×10 mL) before it was suction filtered dry for ~0.5 hr. A light yellowish-green powder (0.235 g, 86% yield) which analyzed for (Bu$_4$N)$_2$Co(CN)$_4$ · C$_5$H$_5$N was obtained.

FTIR (Nujol): 2099 (w), 2079 (s), 2054 (sh), 2040 (w) cm$^{-1}$ (CN);

1589 (m) cm$^{-1}$ (pyridine).

2124 (w), 2098 (w), 2093 (w), 2078 (s), 2055 (sh), 2041 (w) cm$^{-1}$ (CN, after exposure to air).

Elemental Analysis (Found): Co, 7.72; C, 67.62; H, 10.51; N, 13.79.

Expected for (Bu$_4$N)$_2$Co(CN)$_4$ · C$_5$H$_5$N: Co, 8.10; C, 67.73; H, 10.68; N, 13.48.

A second batch of (Bu$_4$N)$_2$Co(CN)$_4$ · C$_5$H$_5$N (1.261 g, 92% yield) was prepared by the same procedure but at five times the scale.

TGA Studies of the Reversible Oxygen Binding Behavior of (Bu$_4$N)$_2$Co(CN)$_4$ · C$_5$H$_5$N:

A sample of (Bu$_4$N)$_2$Co(CN)$_4$ · C$_5$H$_5$N was loaded on a Perkin-Elmer TGA (under nitrogen). No weight loss occurred at 30° C. under nitrogen (30 min). On switching to oxygen (10 min), a weight gain of 3.25% was observed. Under nitrogen, a weight loss of 3.38% was seen after 30 min, and a second oxygenation resulted in a 3.84% weight gain. Subsequently, a total of 25 cycles were performed with excellent reversible oxygen binding (see Table 1). Interestingly, the color of the material changed from green to red on exposure to oxygen and changed back to green under nitrogen after ~15-20 minutes.

TABLE 1

Reversible Oxygen Binding Behavior of (Bu$_4$N)$_2$Co(CN)$_4$·C$_5$H$_5$N
(Cycle = Oxygen 10 min/Nitrogen 30 min)

| Cycle Number | Wt. Gain Under O$_2$ | Wt. Loss Under N$_2$ |
| --- | --- | --- |
| 1 | 3.25% | 3.38% |
| 2 | 3.84% | 3.91% |
| 3 | 3.97% | 4.00% |
| 4 | 3.99% | 4.04% |
| 8 | 3.91% | 3.94% |
| 12 | 3.79% | 3.80% |
| 15 | 3.67% | 3.71% |
| 20 | 3.55% | 3.58% |
| 24 | 3.44% | 3.50% |
| 25 | 3.42% | — |

A fresh sample of (Bu$_4$N)$_2$Co(CN)$_4$ · C$_5$H$_5$N was oxygenated for 60 minutes and a weight gain of 3.97% (90% of the calculated stoichiometric uptake for (Bu$_4$N)$_2$Co(CN)$_4$ · C$_5$H$_5$N) was seen after ~30 minutes. Desorption under nitrogen for 90 minutes resulted in a 4.14% weight loss. Subsequent cycling looked similar to that shown above.

EXAMPLE 5

Synthesis and Elemental Analysis of [(Bu$_4$N)$_2$Co(CN)$_4$]$_2$ · (4.4'-dipyridyl)

(Bu$_4$N)$_2$Co(CN)$_4$ (0.628 g, 0.969 mmol) was dissolved in anhydrous DMF (10 mL); a deep blue-green solution resulted. Then a solution of 4,4'-dipyridyl (0.300 g, 1.92 mmol) in DMF (15 mL) was added to the (Bu$_4$N)$_2$Co(CN)$_4$ solution at room temperature with stirring. The color changed to orange. After fifteen minutes at room temperature, the product was precipitated by adding diethyl ether (75 mL) to the DMF solution. The orange solid was filtered and washed thoroughly with fresh ether (3×25 mL) before it was suction filtered dry for ~1 hr. An orange powder (0.598 g, 85% yield) which analyzed for [(Bu$_4$N)$_2$Co(CN)$_4$]$_2$ · (4,4'-dipyridyl) was obtained.

FTIR (Nujol): 2101 (w), 2081 (s), 2043 (w) cm$^{-1}$ (CN).

2113 (m), 2102 (w), 2081 (s), 2042 (vw) cm$^{-1}$ (CN, after exposure to air); 1127 (m) cm$^{-1}$ (Co(lll) superoxo).

Elemental Analysis (Found): Co, 8.12; C, 67.78; H, 9.49; N, 13.84

Calc'd for: Co, 8.12; C, 67.83; H, 10.55; N, 13.50 [(Bu$_4$N)$_2$Co(CN)$_4$]$_2$ · C$_{10}$H$_8$N$_2$ TGA Studies of the Reversible Oxygen Binding Behavior of [(Bu$_4$N)$_2$Co(CN)$_4$]$_2$ · C$_{10}$H$_8$N$_2$ TGA studies were done on [(Bu$_4$N)$_2$Co(CN)$_4$]$_2$ · C$_{10}$H$_8$N$_2$ using a DuPont TGA which has 100% oxygen purging on oxygenation. Interestingly, this material has a relatively rapid component and a very slow component; the rapid component uptakes ~2.3% by weight in 15 minutes and the slow component gains an additional ~1.4% by weight over 465 minutes. Desorption, on the other hand, occurs very rapidly: 3.8% in ~20 minutes. Although the total capacity was never reached after 480 minutes under oxygen, the fast component could easily be accessed with cycles consisting of 15 minutes under oxygen and 20 minutes under nitrogen at 30° C. The material was cycled 101 times (Oxygen 15 min/nitrogen 20 min) at 30° C. were performed. The weight gain observed on oxygenation did not diminish over the 101 cycles (see Table 2 below).

TABLE 2

Reversible Oxygen Binding Behavior of
[(Bu₄N)₂Co(CN)₄]₂·C₁₀H₈N₂
(Cycle = Oxygen 15 min/Nitrogen 20 min) on DuPont TGA

| Cycle Number | Wt. Gain Under $O_2$ | Wt. Loss Under $N_2$ |
|---|---|---|
| 1 | 2.4% | 2.2% |
| 2 | 2.3% | 2.6% |
| 3 | 2.5% | 2.6% |
| 4 | 2.4% | 2.6% |
| 5 | 2.4% | — |
| 10 | 2.4% | — |
| 20 | 2.4% | — |
| 30 | 2.41% | — |
| 40 | 2.44% | — |
| 50 | 2.48% | — |
| 60 | 2.47% | — |
| 70 | 2.49% | — |
| 80 | 2.48% | — |
| 90 | 2.49% | — |
| 100 | 2.51% | 2.53% |
| 101 | 2.48% | — |

EXAMPLE 6

Synthesis of [(Bu₄N)₂Co(CN)₄]₂ · C₄H₄N₂

(Bu₄N)₂Co(CN)₄ (0.302 g, 0.466 mmol) was dissolved in anhydrous DMF (20 mL); a deep blue-green solution resulted. Then a solution of pyrazine (0.123 g, 1.54 mmol) in DMF (10 mL) was added to the (Bu₄N)₂Co(CN)₄ solution at room temperature with stirring. The color changed to orange. After fifteen minutes at room temperature, precipitation of the product was attempted; however, the product was very soluble. Successful isolation of the product was only achieved by adding a very large volume of diethyl ether (150–200 mL) to the DMF solution. The yellow-orange solid was filtered and washed thoroughly with fresh ether (4×20 mL) before it was suction filtered dry for ~2 hr. A yellowish-orange powder (0.280 g) which analyzed for [(Bu₄N)₂Co(CN)₄]₂ · C₄H₄N₂ was obtained.

FTIR (Nujol): 2116 (w), 2104 (sh), 2095 (sh), 2084 (s), 2045 (w) cm⁻¹ (CN)

2116 (m), 2105 (w), 2084 (s) cm⁻¹ (CN, after exposure to air); 1128 (m) cm⁻¹ (Co(III) superoxo).

Elemental Analysis (Found): Co, 9.04; C, 66.29; H, 10.38; N, 13.83

Calc'd for: Co, 8.56; C, 66.34; H, 10.84; N, 14.25 (Bu₄N)₂Co(CN)₄]₂ · C₄H₄N₂

TGA Studies of the Reversible Oxygen Binding Behavior of [(Bu₄N)₂Co(CN)₄]₂ · C₄H₄N₂:

A sample of [(Bu₄N)₂Co(CN)₄]₂ · C₄H₄N₂ was loaded on a Perkin-Elmer TGA (under nitrogen). No weight loss occurred at 30° C. under nitrogen (10 min). On switching to oxygen (10 min), a weight gain of 2.87% was observed, followed by a very small weight loss while the sample was still under oxygen. Under nitrogen, a weight loss of 2.14% was seen after 25 min (weight loss had leveled off long before 25 min was reached), and a second oxygenation resulted in a 1.82% weight gain. Subsequently, a total of 30 cycles were performed with reasonable reversible oxygen binding (see Table 3).

TABLE 3

Reversible Oxygen Binding Behavior of
[(Bu₄N)₂Co(CN)₄]₂·C₄H₄N₂
(Cycle = Oxygen 10 min/Nitrogen 30 min)

| Cycle Number | Wt. Gain Under $O_2$ | Wt. Loss Under $N_2$ |
|---|---|---|
| 1 | 2.87% | 2.14% |
| 2 | 1.82% | 1.61% |
| 3 | 1.15% | 1.00% |
| 13 | 0.60% | 0.62% |
| 14 | 0.59% | 0.59% |
| 15 | 0.57% | 0.58% |
| 29 | 0.30% | 0.31% |
| 30 | 0.29% | — |

EXAMPLE 7

Synthesis of [(Bu₄N)₂Co(CN)₄] · C₄H₆N₂

(Bu₄N)₂Co(CN)₄ (0.313 g, 0.483 mmol) was dissolved in anhydrous 1-methylimidazole (5 mL); a greenish-yellow solution resulted. After five minutes at room temperature, anhydrous THF (20 mL) and anhydrous hexane (20 mL) were added to crash out a green oil. On vigorously stirring the mixture for ~10 minutes, a fluffy light green powder resulted. The powder was filtered and washed thoroughly with hexane (10 mL) and diethyl ether (2×10 mL) before it was suction filtered dry for ~3.5 hr. A light green powder (0.281 g, 80% yield) which analyzed for [(Bu₄N)₂Co(CN)₄] · C₄H₆N₂ was obtained.

FTIR (Nujol): 2170 (vw), 2100 (w), 2088 (sh), 2078 (s), 2053 (sh), 2039 (w) cm⁻¹ (CN)

2110 (w), 2089 (sh), 2078 (s), 2053 (sh), 2039 (w) cm⁻¹ (CN, after exposure to air).

Elemental Analysis (Found): Co, 7.81; C, 66.14; H, 10.39; N, 15.56.

Expected for: Co, 8.07; C, 65.81; H, 10.77; N, 15.35. [(Bu₄N)₂Co(CN)₄] · C₄H₆N₂

TGA Studies of the Reversible Oxygen Binding Behavior of [(Bu₄N)₂Co(CN)₄] · C₄H₆N₂

A sample of [(Bu₄N)₂Co(CN)₄] · C₄H₆N₂ was loaded on a Perkin-Elmer TGA (under nitrogen). No weight loss occurred at 30° C. under nitrogen (30 min). On switching to oxygen (10 min), a weight gain of 3.15% was observed. Under nitrogen, a weight loss of 0.36% was seen after 30 min, and a second oxygenation resulted in a 0.67% weight gain. Subsequently, a total of 12 cycles were performed with reversible oxygen binding (see Table 4). This material uptakes oxygen much faster than it desorbs oxygen at 30° C.

TABLE 4

Reversible Oxygen Binding Behavior of
[(Bu₄N)₂Co(CN)₄]·C₄H₆N₂
(Cycle = Oxygen 10 min/Nitrogen 30 min)

| Cycle Number | Wt. Gain Under $O_2$ | Wt. Loss Under $N_2$ |
|---|---|---|
| 1 | 3.15% | 0.36% |
| 2 | 0.67% | 0.23% |
| 3 | 0.28% | 0.18% |
| 8 | 0.17% | 0.17% |
| 11 | 0.18% | 0.16% |
| 12 | 0.14% | — |

If this material is heated to 100° C. for 60 minutes (under nitrogen) and temperature swing cycling is done ($O_2$: 10 min at 30° C./$N_2$: 5 min at 30° C., 5° C./min to 70° C., 70° C. for 30 min, 10° C./min to 30° C., 30° C. for 20 min), completely reversible cycles can be attained.

EXAMPLE 8

Synthesis of Amberlyst A-26 · Co(CN)$_4$ · nDMF

This reaction demonstrates that the cations of (Bu$_4$N)$_2$Co(CN)$_4$ can be exchanged with those of an anion exchange resin to produce a reversible oxygen binding material. Amberlyst A-26 ® is a quaternary ammonium anion exchange resin which has a surface area of 28 m$^2$/g and an ion exchange capacity of 4.4 meq/g; it has a maximum operating temperature of 75° C. Before use in this reaction, the Amberlyst A-26 was dried at room temperature and ~150 millitorr for ~15 hours.

(Bu$_4$N)$_2$Co(CN)$_4$ (0.355 g, 0.548 mmol) was dissolved in anhydrous DMF (5 mL): This solution was added to a slurry of Amberlyst A-26 (1.053 g dry, 4.6 meq) which had been allowed to swell in DMF (10 mL) for 0.5 hour. Additional DMF (5 mL) was used to ensure complete transfer. After 30 minutes at room temperature, the blue color had somewhat dissipated. The green polymer beads were filtered and washed with fresh DMF (2×10 mL) to yield colorless filtrates; after washing with ether (3×15 mL), the polymer was suction filtered dry for ~1.5 hr. Green polymer beads (1.098 g) were obtained. Percent Co: 1.84%.

TGA Studies of the Reversible Oxygen Binding Behavior of Amberlyst A-26 · Co(CN)$_4$ · nDMF A sample of Amberlyst A-26 · Co(CN)$_4$ nDMF was loaded on a Perkin-Elmer TGA (under nitrogen). Weight loss occurred at 30° C. under nitrogen (0.59% in 30 min). On switching to oxygen for 10 minutes, a weight gain of 0.61% was seen, followed by a steep weight loss while still under oxygen. Two more cycles were performed with weight loss constantly occurring except during the first minute under oxygen; weight gains were decreasing in size with each cycle (see Table 5). The sample was then heated to 50° C. for 60 minutes and a total weight loss (from t=O) of 4.75% was seen. Oxygen (10 min)/ nitrogen (30 min) cycling at 30° C. then showed very small weight gains on oxygenation and still showed weight loss during the latter ~8 minutes under oxygen.

TABLE 5

Reversible Oxygen Binding Behavior of Amberlyst A-26.Co(CN)$_4$.nDMF
Before and After Heating to 50° C. for 60 Minutes
(Cycle = Oxygen 10 min/Nitrogen 30 min)

| Cycle Number | Wt. Gain Under $O_2$ | Wt. Loss Under $N_2$ |
|---|---|---|
| 1 | 0.61% | 0.60% |
| 2 | 0.10% | 0.40% |
| 3 | 0.07% | 0.28% |
| sample heated to 50° C. for 60 minutes | | |
| 4 | 0.14% | 0.18% |
| 2 | 0.05% | 0.13% |
| 10 | 0.04% | 0.11% |

EXAMPLE 9

Synthesis of (Bu$_4$N)$_2$Co(CN)$_4$ Supported on Poly(4-vinylpyridine)

Poly(4-vinylpyridine), crosslinked, was purchased from Scientific Polymer Products, Inc. It was dried under vacuum (~100 millitorr) at room temperature for 16 hours and then at 50° C. and 50 millitorr for 24 hours.

A solution of (Bu$_4$N)$_2$Co(CN)$_4$ (0.512 g, 0.790 mmol) in DMF (5 mL) was added to dry poly(4-vinylpyridine) (1.298 g, 12.23 mmol 4-vinylpyridine) with stirring. A concentrated mixture which contained very little liquid (<1 mL) resulted. The mixture was stirred and warmed on a hot plate (~65° C.) to drive off the residual solvent, and then the khaki green polymer beads were dried in an open beaker at room temperature overnight. The next day the polymer was further dried by suction filtering the beads for ~1 hr. Finally the beads were washed with diethyl ether (3×10 mL) and suction filtered dry for ~5 hours. Khaki green polymer beads (1.902 g) were obtained.

The fact that the polymer is green rather than blue suggests that the 4-vinylpyridine units are interacting with the Co(CN)$_4^{2-}$ species. A reasonable loading appears to have been achieved. Percent Co =2.18%.

TGA Studies of the Oxygen Binding Behavior of the Khaki Green Polymer Prepared Above A sample of the material prepared above was loaded on a Perkin-Elmer TGA (under nitrogen). Weight loss occurred at 30° C. under nitrogen (0.43% over 30 min). On switching to oxygen (10 min), a 0.20% weight gain was observed. Oxygen/nitrogen cycling was continued for 18 cycles at 30° C. (Table 6). The material does reversibly bind oxygen, but it continually loses solvent and activity (presumably because less cobalt sites become available as the polymer shrinks). Many sites must be unavailable even during the first cycle (probably not on the surface) since, theoretically, if all of the cobalt has reacted, a 1.3% weight gain should have been observed.

TABLE 6

Reversible Oxygen Binding Behavior of
(Bu$_4$N)$_2$Co(CN)$_4$.poly(4-vinylpyridine)
(Cycle = Oxygen 10 min/Nitrogen 30 min)

| Cycle Number | Wt. Gain Under $O_2$ | Wt. Loss Under $N_2$ |
|---|---|---|
| 1 | 0.20% | 0.50% |
| 2 | 0.10% | 0.29% |
| 3 | 0.12% | 0.18% |
| 10 | 0.08% | 0.16% |
| 15 | 0.08% | 0.13% |
| 18 | 0.07% | 0.11% |

EXAMPLE 10 (COMPARATIVE)

Synthesis of "Cs$_2$Co(CN)$_4$ · 0.84 DMF"

Cesium triflate was prepared by mixing methanolic solutions of cesium chloride (3.1 mmol) and silver triflate (2.6 mmol). The silver chloride that precipitated was filtered off through Celite and the filtrate was evaporated to dryness. The cesium triflate (with unreacted cesium chloride still present) was taken up in DMF (125 ml) and filtered to yield a solution of clean cesium triflate which was used in the subsequent reaction.

(Bu$_4$N)$_2$Co(CN)$_4$ (0.440 g, 0.679 mmol) was dissolved in anhydrous DMF (10 mL). This solution was added to the filtered solution of cesium triflate in DMF (125 mL). Additional DMF (5 mL) was used to ensure complete transfer. The color of the cobalt mixture became a pale brownish-yellow and very fine precipitate came out of solution. The mixture was unsuccessfully filtered, and then 50 mL of diethyl ether were added in order to coagulate the product. Filtration then yielded a dark brown sludge which was washed with DMF (10 mL), diethyl ether (20 mL), and hexane (2×10 mL) to yield a brown powder. The sample was suction filtered dry for ~1 hour to yield 0.268 g of material.

FTIR (Nujol): 2105 (s), 2086 (s), 2046 (sh) cm$^{-1}$ (CN); 1659 (s) cm$^{-1}$ (DMF)

2183 (sh), 2122 (sh), 2105 (s), 2086 (s) cm$^{-1}$ (CN, after exposure to air); no Co(III) superoxo stretch was seen Elemental Analysis (Found): Co, 12.0; Cs, 54.8 Cs/Co ratio=2.02

Calc'd for $Cs_2Co(CN)_4 \cdot 0.84$ DMF: Co, 12.02; Cs, 54.22

TGA Studies of the Oxygen Binding Behavior of "$Cs_2Co(CN)_4 \cdot 0.84$ DMF"

A sample of "$Cs_2Co(CN)_4 \cdot 0.84$ DMF" was loaded on a Perkin-Elmer TGA (under nitrogen). Weight loss occurred at 30° C. under nitrogen (0.36% in 30 min). On switching to oxygen for 20 minutes, a weight gain of 1.04% was seen. Unfortunately, desorption under nitrogen was extremely small (0.09% in 30 minutes). Therefore, the sample was heated to 80° C. for 30 minutes; only a 1.23% weight loss was seen. Oxygenation at 30° C. for 20 minutes resulted in a 0.18% weight gain but only a 0.05% weight loss was seen when the sample was purged with nitrogen while heating to 50° C. for 30 minutes. Finally, the sample was heated to 160° C. for 30 minutes and a weight loss of 2.04% was seen before a plateau and no further weight loss was seen. Oxygenation at 30° C. then resulted in a 0.24% weight gain, but no weight loss was seen under nitrogen on heating to 120° C. for ~15 minutes. This material appears to be an irreversible oxygen binder.

EXAMPLE 11 (COMPARATIVE)

Attempted Synthesis of "$Cs_2Co(CN)_4 \cdot x\ C_5H_5N$"

This reaction was attempted because it was hoped that the Cs$^+$ cation would be more stable than the Bu$_4$N$^+$ cation, thus producing a more stable reversible oxygen binding material, and it was hoped that having a pyridine axial base would allow an "open" enough structure for reversible oxygen binding to take place.

Cesium triflate was prepared by mixing methanolic solutions of cesium chloride (3.94 mmol) and silver triflate (3.31 mmol). The silver chloride that precipitated was filtered off through Celite and the filtrate was evaporated to dryness. The cesium triflate (with unreacted cesium chloride still present) was taken up in DMF (75 ml) and filtered to yield a solution of clean cesium triflate which was used in the subsequent reaction.

The filtered solution of cesium triflate in DMF (75 mL) was added to a solution of $(Bu_4N)_2Co(CN)_4$ (0.564 g, 0.870 mmol) in anhydrous pyridine (15 mL). Additional DMF (10 mL) was used to ensure complete transfer. The color of the cobalt mixture became a pale brownish-yellow and very fine precipitate came out of solution. The mixture was unsuccessfully filtered, and then ~100 mL of diethyl ether were added in order to coagulate the product after stirring overnight. Filtration then yielded a fine brown powder which was washed with fresh ether (3×20 mL) and suction filtered dry for ~1.5 hour to yield 0.235 g of beige powder.

FTIR (Nujol): 2104 (s), 2088 (s), 2048 (sh) cm$^{-1}$ (CN); 1658 (s) cm$^{-1}$ (DMF); 1591 (w) cm$^{-1}$ (pyridine?)

2183 (sh), 2146 (sh), 2124 (sh), 2107 (s), 2088 (s) cm$^{-1}$ (CN, after exposure to air); no Co(III) superoxo stretch was seen TGA Studies of the Oxygen Binding Behavior of "$Cs_2Co(CN)_4 \cdot x\ DMF \cdot y\ C_5H_5N$"

A sample of "$Cs_2Co(CN)_4 \cdot x\ DMF \cdot y\ C_5H_5N$" was loaded on a Perkin-Elmer TGA (under nitrogen). No weight loss occurred at 30° C. under nitrogen. On switching to oxygen for 10 minutes, a weight gain of 1.40% was seen. Unfortunately, desorption under nitrogen was extremely small (0.04% in 30 minutes). Therefore, the sample was heated to 50° C. for 60 minutes; only a 0.27% weight loss was seen. Oxygenation at 30° C. for 20 minutes resulted in no weight gain. Finally, the sample was heated to 120° C. for 60 minutes and a weight loss of 0.93% was seen before a plateau and no further weight loss was seen. Oxygenation at 30° C. then resulted in a 0.3% weight gain, but no weight loss was seen under nitrogen at 30° C. for 30 minutes. When the sample was heated to 100° C. under nitrogen for 30 minutes, no weight loss was seen. This material also appears to be an irreversible oxygen binder.

Having thus described the present invention, what is now deemed appropriate for Letters Patent is set out in the following appended claims.

We claim:

1. A solid state composition comprising one or more cyanocobaltate complexes represented by the chemical formula:

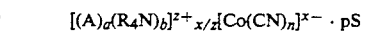

$[(A)_a(R_4N)_b]^{z+}{}_{x/z}[Co(CN)_n]^{x-} \cdot pS$ where:

A is alkali metal atom, alkaline earth metal atom, Zn, Cd or Hg atom;

a is any number from 0 to 2.5 each R is independently $C_1-C_{10}$ substituted or unsubstituted alkyl, aryl or aralkyl; or a long chain hydrocarbon polymer b is any number from greater than zero to 3 z is 1, 2 or 3;

n is any number from 3 to 5;

x is n−2;

p is any number from greater than zero to 6; and

S is a ligand which is capable of coordinating with $[(A)_a(R_4N)_b]^{z+}$, Co, or both.

2. The composition of claim 1 wherein S is selected from the group consisting of N,N-dialkyl amides, alkyl lactams, N-alkyl imides, ammonia, acetone, chelating tertiary amines, N-heterocycles, organic nitriles, polymers containing polyvinylpyridine or pyrrolidone, cyanamide anion, dicyanamide anion, dicyanomethane anion, halide ions, SCN$^-$, NCS$^-$, and mixtures thereof.

3. The composition of claim 1 wherein S is an organic amide.

4. The composition of claim 3 wherein S is selected from the group consisting of N,N-dimethylformamide, N-methyl-2-pyrrolidinone, N,N-dimethylacetamide and mixtures thereof.

5. The composition of claim 4 wherein p is number from 2 to 3.

6. The composition of claim 1 wherein n is 5.

7. The composition of claim 1 wherein R is a butyl group.

8. The composition of claim 1 wherein R is an ethyl group.

9. The composition of claim 1 wherein "a" is zero.

10. The composition of claim 9 wherein R is an ethyl group, butyl group, or a benzyl group.

11. The composition of claim 9 wherein S is 4,4'-dipyridyl.

12. The composition of claim 1 wherein A is Li.

13. The composition of claim 1 wherein A is Na.

14. The composition of claim 1 wherein S is acetone.

* * * * *